(12) United States Patent
Jones et al.

(10) Patent No.: US 11,202,755 B2
(45) Date of Patent: Dec. 21, 2021

(54) PHARMACEUTICAL COMPOSITIONS

(71) Applicant: UniWell Laboratories, LLC, Fort Worth, TX (US)

(72) Inventors: Alan Jones, Argyle, TX (US); Cesar Rodriguez, Prosper, TX (US); David Henzler, Haslet, TX (US); Jeff Currington, Corinth, TX (US); Megha Sharma, Lewisville, TX (US); Daniel Aldrich, Bedford, TX (US); Cameron Currington, Corinth, TX (US); Michael Sloane, Fort Worth, TX (US)

(73) Assignee: UniWell Laboratories, LLC, Fort Worth, TX (US)

( * ) Notice: Subject to any disclaimer, the term of this patent is extended or adjusted under 35 U.S.C. 154(b) by 0 days.

(21) Appl. No.: 15/507,976

(22) PCT Filed: Feb. 21, 2016

(86) PCT No.: PCT/US2016/018832
§ 371 (c)(1),
(2) Date: Mar. 1, 2017

(87) PCT Pub. No.: WO2017/007515
PCT Pub. Date: Jan. 12, 2017

(65) Prior Publication Data
US 2018/0177719 A1    Jun. 28, 2018

Related U.S. Application Data

(60) Provisional application No. 62/190,650, filed on Jul. 9, 2015.

(51) Int. Cl.
| | |
|---|---|
| *A61K 9/00* | (2006.01) |
| *A61K 9/06* | (2006.01) |
| *A61K 47/32* | (2006.01) |
| *A61K 31/09* | (2006.01) |
| *A61K 31/137* | (2006.01) |
| *A61K 31/138* | (2006.01) |
| *A61K 31/167* | (2006.01) |
| *A61K 31/4045* | (2006.01) |
| *A61K 31/4402* | (2006.01) |
| *A61K 31/485* | (2006.01) |
| *A61K 47/02* | (2006.01) |
| *A61K 47/10* | (2017.01) |
| *A61K 47/14* | (2017.01) |
| *A61K 47/18* | (2017.01) |
| *A61K 47/26* | (2006.01) |
| *A61K 47/34* | (2017.01) |
| *B65D 75/36* | (2006.01) |

(52) U.S. Cl.
CPC ............ *A61K 9/0056* (2013.01); *A61K 9/06* (2013.01); *A61K 31/09* (2013.01); *A61K 31/137* (2013.01); *A61K 31/138* (2013.01); *A61K 31/167* (2013.01); *A61K 31/4045* (2013.01); *A61K 31/4402* (2013.01); *A61K 31/485* (2013.01); *A61K 47/02* (2013.01); *A61K 47/10* (2013.01); *A61K 47/14* (2013.01); *A61K 47/183* (2013.01); *A61K 47/26* (2013.01); *A61K 47/32* (2013.01); *A61K 47/34* (2013.01); *B65D 75/36* (2013.01)

(58) Field of Classification Search
CPC .... A61K 9/0056; A61K 9/0095; A61K 47/26; A61K 47/32
See application file for complete search history.

(56) References Cited

U.S. PATENT DOCUMENTS

| | | | | |
|---|---|---|---|---|
| 4,818,517 | A | | 4/1989 | Kwee et al. |
| 5,300,302 | A | * | 4/1994 | Tachon ................. A61K 9/0095 424/488 |
| 5,881,926 | A | * | 3/1999 | Ross ..................... A61J 7/0023 141/114 |
| 6,165,512 | A | * | 12/2000 | Mezaache ............ A61K 9/0056 424/464 |
| 6,663,893 | B2 | * | 12/2003 | Corbo .................. A61K 9/5015 424/464 |
| 2005/0143471 | A1 | * | 6/2005 | Gao ..................... A61K 9/0056 514/649 |

(Continued)

OTHER PUBLICATIONS

Martindale The Extra Pharmacopoeia, Reynolds (ed.), 13th edition, The Pharmaceutical Press, London, pp. 681, 1136 (1993).*

(Continued)

*Primary Examiner* — John Pak
(74) *Attorney, Agent, or Firm* — Winstead PC

(57) ABSTRACT

By individually metering and dispensing specific volumes and/or weights of each component of a dosage, an amount of the components for each dose is secured with very high accuracy. A method for dosing a pharmaceutical product in a sealed container, such as, for example, a packet, sachet, blister pack, or other unit dose form. The dosage may include a first component that is a thickening agent and a second component that is an active ingredient. The thickening agent serves as a carrier that allows the active ingredient to dissolve in the mouth and be swallowed without the administration of water. The method includes providing the first component by measuring the volume or weighing the mass of the first component and measuring the volume or weighing the mass of the second component. Subsequent components may also be individually measured or weighed before being added to a package.

9 Claims, No Drawings

(56) References Cited

U.S. PATENT DOCUMENTS

2010/0063010 A1* 3/2010 Mehta .................. A61J 7/0023
514/165
2011/0061345 A1 3/2011 Cherukuri et al.

OTHER PUBLICATIONS

Pharmaceutical Bulletin 6, Lubrizol, pp. 1-8, May 31, 2001.*
Cheatham, R., "Navigating the Landscape of Sweetener Formulations," Food Tech Toolbox, Feb. 2014, pp. 1-7.*
HCAPLUS abstract 2010:1170697; abstracting CN 101829026 (2010).*

* cited by examiner

PHARMACEUTICAL COMPOSITIONS

CROSS-REFERENCES TO RELATED APPLICATIONS

This application claims the benefit under 35 U.S.C. § 119(e) of U.S. Provisional Patent Application No. 62/190,650, filed Jul. 9, 2015, which is incorporated herein by reference in its entirety as if fully set forth herein.

FIELD OF THE INVENTION

The present invention relates to a solid/semi-solid dosage form packaging for pharmaceutical and dietary supplement compositions.

BACKGROUND OF THE INVENTION

Pharmaceutical and dietary supplement compositions may be produced in a variety of dosage forms, depending upon the desired route of administration of the active ingredient. Oral dosage forms, for example, include such solid/semi-solid compositions as tablets, granules, powders, beads, minitablets, and pellets. The particular dosage form utilized will depend on such factors as the solubility and chemical reactivity of the active ingredient. Further, the dosage form may be selected so as to optimize delivery of the active ingredient and/or consumer acceptability of the composition.

Additionally, accuracy of the doses is of importance. Pharmaceutical compositions often contain active drug components that are harmful if the given dose is too high. On the other hand, the desired effect of the medicament is not achieved if the dose is too low.

When two or more ingredients are contained in a dosage form, uniform mixing of the ingredients prior to packaging is important in maintaining consistency and accuracy of the doses. It is, however, difficult to uniformly mix two or more solid ingredients having different physical characteristics, such as particle size, density, and flowability, as the ingredients tend to separate.

Therefore, a need remains for providing consistent and accurate pharmaceutical dosages, especially for rapid melt dosages. Such compositions are ideal for uses in the fields of pediatric and geriatric care, that is, for use with people or mammals who have severe health issues, who cannot swallow the tablet or capsule, and people who do not have any teeth. Such compositions can also be used in the cancer patients. Such compositions can be administered without water.

SUMMARY OF THE INVENTION

By individually metering and dispensing specific volumes and/or weights of each component of a dosage, an amount of the components for each dose is secured with very high accuracy. Thus, one of the advantages with the present invention is that the accuracy and precision of the amount of the components can be monitored and metered, and the result used to secure the quality of the pharmaceutical product.

The present invention relates to a new method for dosing a pharmaceutical or dietary supplement product in a sealed container, such as, for example, a packet, sachet, or blister pack, comprising a first component and a second component. In some embodiments, the first component is a thickening agent and the second component is an active ingredient. The thickening agent serves as a carrier that allows the active ingredient to dissolve in the mouth and be swallowed without the administration of water. When in use, the user merely opens the container and empties its contents into the mouth. The same principle can be used to make pharmaceutical and dietary supplement products containing more than two components.

The two component dosage form can be packaged in a sealed container, such as, for example, a packet, sachet, blister pack, or other unit dose form. The method comprises providing the first component by measuring the volume or weighing the mass of the first component. Thus, a defined dose of the first component is provided. Further, the method comprises introducing the first component into a package, measuring the volume or weighing the mass of the second component, introducing the second component into the package, and sealing the package. Subsequent components are also individually metered before being added to the package. When all the components are added to the container, it is sealed and ready for use.

DETAILED DESCRIPTION OF EXEMPLARY EMBODIMENTS

In describing and claiming the present invention, the following terminology will be used in accordance with the definitions set forth below. The singular forms "a," "an," and, "the" include plural referents unless the context clearly dictates otherwise. Thus, for example, reference to "a drug" includes reference to one or more of such drugs, and reference to "an excipient" includes reference to one or more of such excipients.

As used herein, the terms "formulation" and "composition" and "component" are used interchangeably and refer to a mixture of two or more compounds, elements, or molecules. In some aspects the terms "formulation" and "composition" may be used to refer to a mixture of one or more active agents with a carrier or other excipients.

As used herein, "active agent," "bioactive agent," "pharmaceutically active agent," "pharmaceutical," "active ingredient," "vitamin or mineral" or "functional agents" variations thereof may be used interchangeably to refer to an agent or substance that has measurable specified or selected physiologic activity when administered to a subject in a significant or effective amount. It is to be understood that the term "drug" is expressly encompassed by the present definition as many drugs and prodrugs are known to have specific physiologic activities. These terms of art are well-known in the pharmaceutical and medicinal arts.

As used herein, "subject" refers to a mammal that may benefit from the administration of a drug composition or method of this invention. Examples of subjects include humans, and may also include other animals such as horses, pigs, cattle, dogs, cats, rabbits, and aquatic mammals.

As used herein, "blood level" may be used interchangeably with terms such as blood plasma concentration, plasma level, plasma concentration, serum level, serum concentration, serum blood level and serum blood concentration. As used herein, "oral dosage form" and the like refers to a formulation that is ready for administration to a subject through the oral route of administration. Examples of known oral dosage forms, include without limitation, tablets, caplets, powders, pellets, granules, beads and mini tablets and combinations thereof etc. Such formulations also include multilayered tablets wherein a given layer may represent a different drug. In some aspects, granules, powders, pellets, minitablets, or nanoparticles may be coated with a suitable polymer/fat/wax/emulsifier/carbohydrate or a conventional coating material to achieve, for example, greater stability in the oral cavity, gastrointestinal tract, to achieve the desired rate of release, or to improve taste. Tablets and caplets may be scored to facilitate division of dosing. Alternatively, the dosage forms of the present invention may be unit dosage forms wherein the dosage form is intended to deliver one therapeutic dose per administration. Particular embodiments or groups of embodiments may be expressly limited to subsets of these dosage forms.

As used herein, "packet" or "stick pack" refers to a small, sealed packet containing a quantity of material, which is a single-use or unit dose quantity.

As used herein, an "effective amount" or a "therapeutically effective amount" of a drug or active ingredient refers to a sufficient amount of the drug, to achieve therapeutic results in treating a condition for which the drug is known to be effective. It is understood that various biological factors may affect the ability of a substance to perform its intended task. Therefore, an "effective amount" or a "therapeutically effective amount" may be dependent in some instances on such biological factors.

As used herein, "pharmaceutically acceptable carrier" and "carrier" may be used interchangeably, and refer to any inert and pharmaceutically acceptable material that has substantially no biological activity, and makes up a substantial part of the formulation. The term "admixed" means that the drug and/or other ingredients can be dissolved, dispersed, or suspended in the carrier. In some cases, the drug may be uniformly admixed in the carrier.

As used herein, the term "substantially" refers to the complete or nearly complete extent or degree of an action, characteristic, property, state, structure, item, or result. For example, an object that is "substantially" enclosed would mean that the object is either completely enclosed or nearly completely enclosed. The exact allowable degree of deviation from absolute completeness may in some cases depend on the specific context. However, generally speaking the nearness of completion will be so as to have the same overall result as if absolute and total completion were obtained. The use of "substantially" is equally applicable when used in a negative connotation to refer to the complete or near complete lack of an action, characteristic, property, state, structure, item, or result. For example, a composition that is "substantially free of" particles would either completely lack particles, or so nearly completely lack particles that the effect would be the same as if it completely lacked particles. In other words, a composition that is "substantially free of" an ingredient or element may still actually contain such item as long as there is no measurable effect thereof. As used herein, the term "about" is used to provide flexibility to a numerical range endpoint by providing that a given value may be "a little above" or "a little below" the endpoint.

The dosage form of the present invention comprises at least a first and a second component that are provided in a sealed container. In some embodiments, the first component is a thickening agent and the second component is an active ingredient, preferably in a powder, granule, bead, minitablet, pellet, nanoparticle, or a combination thereof. The thickening agent acts as a carrier for the active ingredient so that, when the dosage form is placed in the mouth, the active ingredient can be rapidly dissolved and ingested without additional administration of water. Although water is not required to dissolve the active ingredient, in certain embodiments, water may be used to assist in ingestion of the dosage form. Further, the method comprises introducing the first component into a package, metering a desired volume of the second component, introducing the second component into the same package, and sealing the package into which the components have been introduced. Subsequent components can similarly be added to the same package.

In some embodiments, the method comprises sealing the package after introducing the components.

In some embodiments, the present invention provides a solid or semi-solid product comprising at least a first and a second component in the same dosage form. The product can be contained, for example, in a package. Preferably, at least one of the components contains an active ingredient. It is also desirable to have at least one thickening agent. Preferably, the ratio of the active ingredient to a carbomer ranges from 0.001:0.05 to 0.05:0.1.

In some embodiments, the present invention provides a dosage form in a sealed container containing at least two components. The dosage form can be contained, for example, in a package. Preferably, at least one of the components contains an active ingredient and at least one of the other components contains a thickening agent.

The active ingredients can also be modified for taste masking, for a controlled release, or for a sustained release. Sustained and controlled release of the actives can be achieved using polymer coatings such as polyvinyl acetate, ethocel, and copolymers of ethyl acrylate and methyl methacrylate (e.g., Kollicoat® SR or Eudragit® RL/RS) as well as using Ion-Exchange resins to exchange ions in the resin with ions of the active drug (e.g., Dextromethorphan) and further coated with the same sustained release coatings as described above. The taste masking of the active ingredients can be achieved with polymers (methacrylate polymers, cellulose polymers, or combinations thereof), resins, fats, waxes, or carbohydrates. Processes for taste masking of the active ingredients include granulation, complexation, spray congealing, spray drying and fluid bed coating, which are known in the art.

The amount of active ingredient in the preparation is in the range of 0.1 mg to 5 g. Preferred prophylactic or therapeutic active ingredients contemplated for use in the present inventive subject matter are, without limitation, guaifenesin, mesalamine, diltiazem, metoprolol, balsalazide, aspirin, benzocaine, diphenhydramine, acetaminophen, ibuprophen and mixtures thereof. Preferred prophylactic or therapeutic active ingredients contemplated for use in the present inventive subject matter are antibiotic, which is selected from the group consisting of amoxicillin and clavulanate potassium, ciprofloxacin HCl, azithromycin, clarithromycin, sterile ceftriaxone sodium, cefuroxime axetil, imipenem cilastatin, levofloxacin, ceftazidime, ampicillin sodium and sulbactum sodium, cefaclor, amoxicillin, cefdinir, roxithromycin, sterile cefotaxime sodium, vancomycin, piperacillin sodium and tazobactum sodium, morniflumate, flomoxef sodium, cefotiam dihydrochloride, ofloxacin, mupirocin calcium, vancomycin HCl, teicoplanin, cefadroxil monohydrate, sulbactum cefoperazone, meropenem, ofloxacin, cephalexin, cefepime HCl, cefuroxime sodium, minocycline HCl, cefaclor, cefazolin, trimethoprim and sulfamethoxazole, norfloxacin, trovafloxacin, cefpodoxime proxetil, cefdinir, cefixime, panipenem, ceftibuten, levofloxacin, cefoxopran HCl, amikacin sulfate, aztreonam, minocycline HCl, ticarcillin disodium or mixtures thereof.

Many of the active ingredients listed above have unpalatable tastes. Taste-masking of compositions with those unpalatable active materials is well-known in the art. The active ingredient may be coated with a suitable polymer/fat/wax/emulsifier/carbohydrate. The use of flavors and sweeteners to mask the unpalatability of the active materials is also well-known. Thus, other materials which can be incorporated into composition include flavors, colors, and sweeteners. Importantly, it is possible to incorporate high levels of flavors, sweeteners and other taste-masking agents, making the compositions more palatable when undesirable tastes accompany the active materials. Taste masking may be chosen from natural and synthetic flavor liquids. Flavors useful include, without limitation, volatile oils, synthetic flavor oils, flavoring aromatics, oils, liquids, oleoresins or extracts derived from plants, leaves, flowers, fruits, stems and combinations thereof. A non-limiting list of examples include citrus oils, such as, for example, lemon, orange, grape, lime and grapefruit and fruit essences including apple, pear, peach, grape, strawberry, raspberry, cherry, plum, pineapple, apricot or other fruit flavors.

Taste masking of the active ingredients can be done using the well-known processes in the art such as fluidization, spray drying, spray congealing, complex co-acervation, resin complexation, matrix granulation using carbohydrates, resins, polymers, waxes, and fats.

Taste enhancers may be chosen from natural and synthetic flavor liquids. Useful flavors include, without limitation, volatile oils, synthetic flavor oils, flavoring aromatics, oils, liquids, oleoresins or extracts derived from plants, leaves, flowers, fruits and fruit essences (e.g., apple, pear, peach, grape, strawberry, raspberry, cherry, plum, pineapple, apricot or other fruit flavors), stems, citrus oils (e.g., lemon, orange, grape, lime and grapefruit), fats, and combinations thereof.

Other useful flavorings include aldehydes and esters such as, for example, benzaldehyde (e.g., cherry, almond), citral (e.g., alphacitral—lemon, lime), neral (e.g., betal-citral—lemon, lime), decanal (e.g., orange, lemon), aldehyde C-8 (e.g., citrus fruits), aldehyde C-9 (e.g., citrus fruits), aldehyde C-12 (e.g., citrus fruits), tolyl aldehyde (e.g., cherry, almond), 2,6-dimethyloctanal (e.g., green fruit), and 2-dodecenal (e.g., citrus, mandarin), and mixtures thereof.

In some embodiments of the invention, the thickening agent serves as the taste masking agent.

The compositions are "storage stable", meaning that the compositions are stable in the absence of special handling procedures. The inventive compositions are stable both prior to packaging and after packaging. Importantly, the inventive compositions maintain their stability and integrity without refrigeration and without humidity controls being implemented during handling, packaging and storing of the products. Additionally, since the compositions exhibit increased integrity and stability, the compositions can be used in most of the current economical packages suitable for a global environment. Further, high temperatures are not needed when processing the packaging and sealing.

Embodiments of the invention are directed to a variety of High Viscosity Liquids (Gels) with OTC Cough & Cold Active Pharmaceutical Ingredients (API's) and/or vitamins and minerals. The products are administered using a single-use stick pack delivered directly into the mouth.

In an embodiment of the claimed invention, the thickening agents that are used in the inventive compositions are carbomer at a range of 0.6-1.2 w/w %. A specific carbomer that may be used is Carbomer 974P at 0.60 to 1.2% w/w. In another embodiment of the invention, the thickening agent is Maltitol and/or high fructose corn syrup at 10 to 40% w/w. In certain embodiments, a small amount of Edetate Disodium (EDTA) may be used as a chealate to keep the carbomer stable during storage to keep the viscosity from decreasing.

Embodiments of the invention use polyethylene glycol (PEG) as a solvent for dissolving Actives and Excipients that are not water soluble or slightly water soluble, e.g., APAP, Diphenhydramine, Brompheniramine Maleate, Melatonin, Methyl and Propyl Paraben. In specific embodiments, PEG 400 is used. Propylene Glycol may be used when the Phenylephrine HCL active is used, but in amounts less than 200 mg/kg/d.

An exemplary manufacturing process is described below:
1. Fill Mixing vessel with water.
2. Add Water soluble Actives and EDTA to step 1.
3. In a suitable container, Add PEG 400.
4. Add insoluble Actives to step 3 and dissolve (i.e., APAP, Melatoin, Brompheniramine maleate, Diphenhydramine HCl).
5. Add preservatives (methyl and Propyl paraben) to step 3 and dissolve.
6. Add Carbomer 974P to step 1 and disperse.
7. Add a taste masking amount of Maltitol and sucralose to step 1.
8. Add flavors to step 1.
9. Add colors to step 1, if applicable.
10. Partially neutralize pH with pH adjusting agent to a pH of 4.0 to 5.5 with sodium Hydroxide.
11. Package into Child resistant stick packs.

Key differences between the claimed invention and existing technology:
A. PEG 400 used in place of higher molecular weight PEG 600 to 1000 for products that do not contain Phenylephrine HCl.
B. Higher concentration of Carbomer (0.60 to 1.2% w/w).
C. No heat to produce the product.
D. Lower pH of 4.0 to 5.5.
E. Our viscosity is higher (30,000 to 60,000 cps).
F. No cellulose derivatives.
G. Chelate such as EDTA used to improve the stability of the carbomer thickening agent.
H. Combination of Maltitol, corn syrup, Sorbitol (also used as a thickening agent) and Sucralose for taste-masking bitter actives.

Properties of the claimed invention include:
1. A composition with a short flow rheology for extruding through a stick-pack orifice of 5 to 10 mm
2. Using a combination of Maltitol and/or corn syrup/Sorbitol and Carbomer as a thickening agent: 0.60 to 1.2% w/w Carbomer; 10 to 40% Maltitol or corn syrup.
3. Comprising a chealate to stabilize the Carbomer.
4. Product is stable for approximately 6 months at 40° C./75 RH, 12 months at 30 C/65 RH, and for 24 months at 25° C./60 RH.
5. Product maintains a viscosity of approximately 30,000 to 60,000 cps after 3 months storage at 40° C./75 RH.
6. Product contains between 0.60 to 1.2% w/w Carbomer or 10 to 40% Maltitol, and/or corn syrup/Sorbitol.
7. Product does not contain a cellulose derivative.
8. Product may be administered using a stick-pack straight to the mouth or squeezed and sucked from a pack.
10. Product is stable for approximately 3 months at 40° C./75 RH, 12 months at 30 C/65 RH, and for 24 months at 25° C./60 RH Without further description, it is believed that one of ordinary skill in the art can, using the preceding description and the following illustrative examples, make and use the present invention. The following examples are given to illustrate the present invention. It should be understood that the invention is not to be limited to the specific conditions or details described in the examples. The formulas for an exemplary list of products are shown in the tables below:

Adult Sleep GEL-Melatonin 5 mg/serving

| Ingredients: | Use | (%)/servings |
|---|---|---|
| Purified Water | Solvent | 50-85 |
| Melatonin | Active Ingredient | 0.01-1.0 |
| Polyethylene Glycol (PEG 400) | Solvent | 2-10 |
| Glycerin | | 5-15 |
| Propyl paraben | Preservatives | 0.01-0.1 |
| Methyl paraben | | 0.05-0.2 |
| Edetate disodium | Chealate to stabilize Carbomer | 0.05-1.5 |
| Carbomer 974 P | Viscosity increasing agent | 0.6-1.2 |
| HF Corn Syrup and/or Sorbitol and/or Maltitol Syrup | Taste-Masking Sweeteners | 10-40 |
| Sucralose | | 0.05-1.0 |
| Flavor | Flavors | 0.1-0.7 |
| Sodium Hydroxide or Potassium Hydroxide (QS to pH 4.0 to 5.5) | pH adjustment | 0.02-0.5 |

Children's Night-Time Cold & Congestion-DPH 12.5 mg, PEH 5 mg/serving

| Ingredients: | Use | (%)/servings |
|---|---|---|
| Purified Water | Solvent | 40-60 |
| Diphenhydramine HCl | Active Ingredient | 0.15-1.0 |
| Phenylephrine HCl | Active Ingredient | 0.02-0.5 |
| Propylene Glycol | Solvent | 2-10 |
| Glycerin | | 5-15 |
| Propyl paraben | Preservatives | 0.01-0.1 |
| Methyl paraben | | 0.05-0.2 |
| Edetate disodium | Chealate to stabilize Carbomer | 0.05-1.5 |
| Carbomer 974 P | Viscosity increasing agent | 0.6-1.2 |
| HF Corn Syrup and/or Sorbitol and/or Maltitol Syrup | Taste-Masking Sweeteners | 10-40 |
| Sucralose | | 0.05-1.0 |
| Flavor | Flavor | 0.1-0.5 |
| FD&C Dye | Color | 0.0001-0.005 |
| Sodium Hydroxide or Potassium Hydroxide (QS to pH 4.0 to 5.5) | pH adjustment | 0.02-0.5 |

Children's Cold & Allergy GEL-BPM 2 mg: PEH 5 mg/serving

| Ingredients: | Use | (%)/servings |
|---|---|---|
| Purified Water | Solvent | 40-65 |
| Brompheniramine Maleate | Active Ingredient | 0.025-0.1 |
| Phenylephrine HCl | Active Ingredient | 0.02-0.5 |
| Glycerin | Solvent | 5-15 |
| Propylene Glycol | | 2-10 |
| Propyl paraben | Preservatives | 0.01-0.1 |
| Methyl paraben | | 0.05-0.2 |
| Edetate Disodium | Chealate to stabilize Carbomer | 0.05-1.5 |
| Carbomer 974 P | Viscosity increasing agent | 0.6-1.2 |
| HF Corn Syrup and/or Sorbitol and/or Maltitol Syrup | Taste-Masking Sweeteners | 10-40 |
| Sucralose | | 0.05-1.0 |
| Flavor | Flavor | 0.1-0.5 |
| FD&C Dye | Colors | 0.0001-0.005 |
| Sodium Hydroxide or Potassium Hydroxide (QS to pH 4.0 to 5.5) | pH adjustment | 0.02-0.5 |

Children's Cough & Cold GEL-DEX 5 mg: PEH 2.5 mg/serving

| Ingredients: | Use | (%)/servings |
|---|---|---|
| Purified Water | Solvent | 40-60 |
| Dextromethorphan HBr | Active Ingredient | 0.05-0.5 |
| Phenylephrine HCl | Active Ingredient | 0.02-0.5 |
| Glycerin | Solvent | 5-15 |
| Propylene Glycol | | 2-10 |
| Propyl paraben | Preservatives | 0.01-0.1 |
| Methyl paraben | | 0.05-0.2 |
| Edetate disodium | Chealate to stabilize Carbomer | 0.05-1.5 |
| Carbomer 974 P | Viscosity increasing agent | 0.6-1.2 |
| HF Corn Syrup and/or Sorbitol and/or Maltitol Syrup | Taste-Masking Sweeteners | 10-40 |
| Sucralose | | 0.05-1.0 |
| Flavor | Flavor | 0.1-0.5 |
| FD&C Dye | Color | 0.0001-0.005 |
| Sodium Hydroxide or Potassium Hydroxide (QS to pH 4.0 to 5.5) | pH adjustment | 0.02-0.5 |

Children's Pain GEL-Acetaminophen 160 mg/serving

| Ingredients: | Use | (%)/servings |
|---|---|---|
| Purified Water | Solvent | 40-65 |
| Acetaminophen | Active Ingredient | 2-3 |
| Polyethylene Glycol (PEG 400) | Solvent | 10-25 |
| Glycerin | | 5-15 |
| Propyl paraben | Preservatives | 0.01-0.1 |
| Methyl paraben | | 0.05-0.2 |
| Edetate Disodium | Chealate to stabilize Carbomer | 0.05-1.5 |
| Carbomer 974 P | Viscosity increasing agent | 0.6-1.2 |
| HF Corn Syrup and/or Sorbitol and/or Maltitol Syrup | Taste-Masking Sweeteners | 10-40 |
| Sucralose | | 0.05-1.0 |
| Flavor | Flavor | 0.1-0.5 |
| Sodium Hydroxide or Potassium Hydroxide (QS to pH 4.0 to 5.5) | pH adjustment | 0.02-0.5 |

Children's Pain GEL-Acetaminophen 240 mg/serving

| Ingredients: | Use | (%)/servings |
|---|---|---|
| Purified Water | Solvent | 40-60 |
| Acetaminophen | Active Ingredient | 3-5 |
| Polyethylene Glycol (PEG 400) | Solvent | 10-25 |
| Glycerin | | 5-15 |
| Propyl paraben | Preservatives | 0.01-0.1 |
| Methyl paraben | | 0.05-0.2 |
| Edetate disodium | Chealate to stabilize Carbomer | 0.05-1.5 |
| Carbomer 974 P | Viscosity increasing agent | 0.6-1.2 |
| HF Corn Syrup and/or Sorbitol and/or Maltitol Syrup | Taste-Masking Sweeteners | 10-40 |
| Sucralose | | 0.05-1.0 |
| Flavor | Flavor | 0.1-0.5 |
| FD&C Dye | Color | 0.0001-0.005 |
| Sodium Hydroxide or Potassium Hydroxide (QS to pH 4.0 to 5.5) | pH adjustment | 0.02-0.5 |

Children's Pain GEL-Acetaminophen 320 mg/serving

| Ingredients: | Use | (%)/servings |
|---|---|---|
| Purified Water | Solvent | 35-55 |
| Acetaminophen | Active Ingredient | 4-6 |
| Polyethylene Glycol (PEG 400) | Solvent | 10-25 |
| Glycerin | | 5-15 |
| Propyl paraben | Preservatives | 0.01-0.1 |
| Methyl paraben | | 0.05-0.2 |
| Edetate Disodium | Chealate to stabilize Carbomer | 0.05-1.5 |
| Carbomer 974 P | Viscosity increasing agent | 0.6-1.2 |
| HF Corn Syrup and/or Sorbitol and/or Maltitol Syrup | Taste-Masking Sweeteners | 10-40 |
| Sucralose | | 0.05-1.0 |
| Flavor | Flavor | 0.1-0.5 |
| FD&C Dye | Color | 0.0001-0.005 |
| Sodium Hydroxide or Potassium Hydroxide (QS to pH 4.0 to 5.5) | pH adjustment | 0.02-0.5 |

Children's MS Cough & Cold GEL-BPM 2 mg: DEX 10 mg: PEH 5 mg/serving

| Ingredients: | Use | (%)/servings |
|---|---|---|
| Purified Water | Solvent | 40-60 |
| Brompheniramine Maleate | Active Ingredient | 0.025-0.1 |
| Dextromethorphan HBr | Active Ingredient | 0.05-0.5 |
| Phenylephrine HCl | Active Ingredient | 0.02-0.5 |
| Glycerin | Solvent | 5-15 |
| Propylene Glycol | | 2-10 |
| Propyl paraben | Preservatives | 0.01-0.1 |
| Methyl paraben | | 0.05-0.2 |
| Edetate Disodium | Chealate to stabilize Carbomer | 0.05-1.5 |
| Carbomer 974 P | Viscosity increasing agent | 0.6-1.2 |
| HF Corn Syrup and/or Sorbitol and/or Maltitol Syrup | Taste-Masking Sweeteners | 10-40 |
| Sucralose | | 0.05-1.0 |
| Flavor | Flavor | 0.1-0.5 |
| FD&C Dye | Color | 0.0001-0.005 |
| Sodium Hydroxide or Potassium Hydroxide (QS to pH 4.0 to 5.5) | pH adjustment | 0.02-0.5 |

Children's Cough & Chest Congestion GEL-GFN 100 mg: DEX 5 mg/serving

| Ingredients: | Use | (%)/servings |
|---|---|---|
| Purified Water | Solvent | 45-65 |
| Guaifenesin | Active Ingredient | 1.0-3.0 |
| Dextromethorphan HBr | Active Ingredient | 0.05-0.5 |
| Polyethylene Glycol (PEG 400) | Solvent | 5-15 |
| Glycerin | | 5-15 |
| Propyl paraben | Preservatives | 0.01-0.1 |
| Methyl paraben | | 0.05-0.2 |
| Edetate disodium | Chealate to stabilize Carbomer | 0.05-1.5 |
| Carbomer 974 P | Viscosity increasing agent | 0.6-1.2 |
| HF Corn Syrup and/or Sorbitol and/or Maltitol Syrup | Taste-Masking Sweeteners | 10-40 |
| Sucralose | | 0.05-1.0 |
| Flavors | Flavors | 0.1-0.5 |
| FD&C Dye | Colors | 0.0001-0.005 |
| Sodium Hydroxide or Potassium Hydroxide (QS to pH 4.0 to 5.5) | pH adjustment | 0.02-0.5 |

Children's Expectorant GEL-GFN 100 mg/serving

| Ingredients: | Use | (%)/servings |
|---|---|---|
| Purified Water | Solvent | 45-65 |
| Guaifenesin | Active Ingredient | 1.0-3.0 |
| Polyethylene Glycol (PEG 400) | Solvent | 5-15 |
| Glycerin | | 5-15 |
| Propyl paraben | Preservatives | 0.01-0.1 |
| Methyl paraben | | 0.05-0.2 |
| Edetate Disodium | Chealate to stabilize Carbomer | 0.05-1.5 |
| Carbomer 974 P | Viscosity increasing agent | 0.6-1.2 |
| HF Corn Syrup and/or Sorbitol and/or Maltitol Syrup | Taste-Masking Sweeteners | 10-40 |
| Sucralose | | 0.05-1.0 |
| Flavors | Flavors | 0.1-0.5 |
| FD&C Dye | Colors | 0.0001-0.005 |
| Sodium Hydroxide or Potassium Hydroxide (QS to pH 4.0 to 5.5) | pH adjustment | 0.02-0.5 |

Children's Cough & Sore Throat

| Ingredients: | Use | (%)/servings |
|---|---|---|
| Purified Water | Solvent | 40-60 |
| Acetaminophen | Active Ingredient | 2-6 |
| Dextromethorphan HBr | Active Ingredient | 0.05-0.5 |
| Polyethylene Glycol (PEG 400) | Solvent | 5-15 |
| Glycerin | | 5-15 |
| Propyl paraben | Preservatives | 0.01-0.1 |
| Methyl paraben | | 0.05-0.2 |
| Edetate Disodium | Chealate to stabilize Carbomer | 0.05-1.5 |
| Carbomer 974 P | Viscosity increasing agent | 0.6-1.2 |
| HF Corn Syrup and/or Sorbitol and/or Maltitol Syrup | Taste-Masking Sweeteners | 10-40 |
| Sucralose | | 0.05-1.0 |
| Flavor | Flavor | 0.1-0.5 |
| FD&C Dye | Colors | 0.0001-0.005 |
| Sodium Hydroxide or Potassium Hydroxide (QS to pH 4.0 to 5.5) | pH adjustment | 0.02-0.5 |

Children's Well Gel Allergy Relief

| Ingredients: | Use | (%)/servings |
|---|---|---|
| Purified Water | Solvent | 50-70 |
| Edetate Disodium | Chealate to stabilize Carbomer | 0.05-1.5 |
| Polyethylene Glycol (PEG 400) and/or Propylene Glycol | Solvent | 5-15 |
| Glycerin | | 5-15 |
| Diphenhydramine HCL | Active Ingredient | 0.15-0.6 |
| Propyl paraben | Preservatives | 0.01-0.1 |
| Methyl paraben | | 0.05-0.2 |

-continued

Children's Well Gel Allergy Relief

| Ingredients: | Use | (%)/servings |
|---|---|---|
| Sucralose | Taste-Masking | 0.05-1.0 |
| HF Corn Syrup and/or Sorbitol and/or Maltitol Syrup | Sweeteners | 10-40 |
| Flavors | Flavor | 0.1-0.5 |
| Carbomer 974 P | Viscosity increasing agent | 0.6-1.2 |
| FD&C Dye | Color | 0.0001-0.005 |
| Sodium Hydroxide or Potassium Hydroxide (QS to pH 4.0 to 5.5) | pH adjustment | 0.02-0.5 |

Children's Well Gel Multi-Symptom Cold & Flu

| Ingredients: | Use | (%)/servings |
|---|---|---|
| Purified Water | Solvent | 30-50 |
| EDTA Disodium | Chealate to stabilize Carbomer | 0.5-1.5 |
| Chlorpheniramine Malate | Active Ingredient | 0.01-0.1 |
| Acetaminophen | Active Ingredient | 2-8 |
| Dextromethorphan HBr | Active Ingredient | 0.06-0.1 |
| Phenylephrine HCL | Active Ingredient | 0.02-0.2 |
| Propylene Glycol | Solvent | 2-10 |
| Glycerin | | 5-15 |
| Propyl paraben | Preservatives | 0.01-0.1 |
| Methyl paraben | | 0.05-0.2 |
| Carbomer 974 P | Viscosity increasing agent | 0.6-1.2 |
| HF Corn Syrup and/or Sorbitol and/or Maltitol Syrup | Taste-Masking Sweeteners | 10-40 |
| Sucralose | | 0.05-1.0 |
| Flavor | Flavor | 0.1-0.5 |
| Sodium Hydroxide or Potassium Hydroxide (QS to pH 4.0 to 5.5) | pH adjustment | 0.02-0.5 |

What is claimed is:

1. A semi-solid oral delivery dosage form packaged in a sealed container, wherein the dosage form comprises:
   a first component that comprises a thickening agent and a thickening agent stabilizer, wherein the thickening agent comprises a carbomer in a range of 0.6 to 1.2% w/w and at least one of maltitol, sorbitol, and corn syrup in a range of 10 to 40% w/w, and wherein the thickening agent stabilizer comprises EDTA or EDTA disodium in a range of 0.6 to 1.2% w/w;
   a second component that comprises a pharmaceutical active ingredient, vitamin and/or mineral;
   a third component that comprises purified water in a range of 35 to 70% w/w; and
   a fourth component that comprises a pH adjusting agent;
   wherein (1) the dosage form contents are mixed together without added heat and contained in a sealed container, (2) the dosage form has a pH that is adjusted to 4.0 to 5.5 prior to being packaged in the sealed container, (3) the dosage form does not contain a cellulose derivative, (4) the weight ratio of the second component to the carbomer ranges from 1:50 to 1:2, (5) the dosage form has a viscosity ranging from 30,000 to 60,000 cps, (6) the dosage form maintains a viscosity of approximately 30,000 to 60,000 cps after 3 months storage at 40° C. at a relative humidity of 75%, and (7) the dosage form is stable for approximately 3 months at 40° C. at a relative humidity of 75%, 12 months at 30° C. at a relative humidity of 65%, and 24 months at 25° C. at a relative humidity of 60%.

2. The dosage form of claim 1, further comprising a solvent, wherein the solvent comprises at least one of purified water, propylene glycol, and polyethylene glycol 400.

3. The dosage form of claim 1, further comprising a preservative, wherein the preservative comprises at least one of propyl paraben and methyl paraben.

4. The dosage form of claim 1, wherein the active ingredient comprises beads, minitablets, pellets, granules, crystals, powder, or combinations thereof.

5. The dosage form of claim 1, wherein the active ingredient is coated with at least one of a polymer, a fat, a wax, an emulsifier, and a carbohydrate.

6. The dosage form of claim 1, wherein the active ingredient comprises at least one of melatonin, n-acetyl-cysteine, diphenhydramine HCl, phenylephrine HCl, brompheniramine maleate, phenylephrine HCl, dextromethorphan HBr, acetaminophen, guaifenesin, chlorpheniramine malate, pseudoephedrine HCl, hydrocodone bitartrate, codeine phosphate, pyrilamine maleate, vitamins, minerals, and herbs.

7. The dosage form of claim 1, wherein the sealed container is a packet, a sachet, a pouch, or a blister pack.

8. The dosage form of claim 1, further comprising a taste masking agent.

9. The dosage form of claim 1, wherein the thickening agent stabilizer comprises EDTA disodium.

* * * * *